United States Patent [19]

Brunke

[11] Patent Number: 4,502,985

[45] Date of Patent: Mar. 5, 1985

[54] USE OF 1,5-DIMETHYL-8-HYDROXIMINO-BICYCLO[3.2.1]OCTANE AS PERFUMING INGREDIENT

[75] Inventor: Ernst-Joachim Brunke, Holzminden, Fed. Rep. of Germany

[73] Assignee: Dragoco Gerberding & Co. GmbH, Holzminden, Fed. Rep. of Germany

[21] Appl. No.: 400,261

[22] Filed: Jul. 21, 1982

[51] Int. Cl.[3] ........................... A61K 7/46; C11B 9/00

[52] U.S. Cl. ................................ 252/522 R; 426/538

[58] Field of Search ...................... 252/522 R; 426/538

[56] References Cited

U.S. PATENT DOCUMENTS 3,637,533 1/1972 Dahill ................................ 252/522

FOREIGN PATENT DOCUMENTS 2043341 3/1971 Fed. Rep. of Germany .

543584 12/1973 Switzerland .

OTHER PUBLICATIONS

Sundt et al., *Helv. Chim. Acta,* 54, 1801, (1971).

Lamparsky et al., Parf. Cosm. Sav. France, vol. 2, No. 11, Nov. 1972, pp. 465–467.

*Primary Examiner*—Joseph Golian

*Attorney, Agent, or Firm*—Anthony J. Casella; Gerald E. Hespos

[57] ABSTRACT

Process for imparting, enhancing or modifying the odorous note in perfumes, perfume compositions, artificial essential oils, flavoring agents or flavor compositions to a "blackcurrant" note, which comprises adding thereto 1.5-dimethyl-8-hydroximino-bicyclo[3.2.1]octane

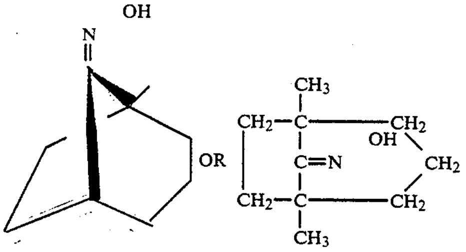

2

Wherein the wavy line denotes geometric isomers, at a concentration of at least 1 part per million by weight based on the total weight of the thus obtained material.

4 Claims, No Drawings

USE OF 1,5-DIMETHYL-8-HYDROXIMINO-BICYCLO[3.2.-1]OCTANE AS PERFUMING INGREDIENT

THE INVENTION

The present invention relates to the field of perfumery and flavoring, in particular it relates to a process for imparting, enhancing or modifying the odorous note in perfumes, perfume compositions, artificial essential oils, flavoring agents or flavor compositions to a "blackcurrant" note, which comprises adding thereto 1.5-dimethyl-8-hydroximino-bicyclo[3.2.1]octane (2) at a concentration of at least 1 part per million by weight based on the total weight of the thus obtained material.

The invention provides a perfume and flavoring composition or an artificial essential oil containing as active perfuming ingredient a compound of formula 2. The invention provides also an artificial essential oil of the "blackcurrant" type or "Cassis bourgeous" which comprises having added thereto a compound of formula 2.

Compound 2 is produced according to a known per se method by reacting 1.5-dimethyl-bicyclo[3.2.1]octane-8-one (1) with hydroxylamine in the presence of a strong base, preferably sodium or potassium acetate or sodium or potassium hydroxide. The production of the ketone 1 and the oxime 2 are described in DE-OS 2 945 812. Nothing was known about olfactory or gustatory properties of the oxime 2

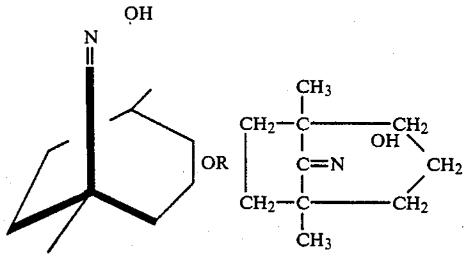

2

BACKGROUND OF THE INVENTION

The expensive "Cassis bourgeous" and, to a greater extent, buchu leaf oil, the essential oil of barosma betulina (Bartl. & Wendl.) have been in use in the perfume and flavoring industry for many years. This oil is available in varying qualities and amounts, but always at a relatively high price. The interesting fragrance complex of buchu leaf oil, with fresh sweet and green-herby notes and a very typical "blackcurrent" character, has prompted various study groups to analyse the oil (E. Sundt, B. Wilhalm, R. Chappaz and G. Ohloff, Helv. Chim. Acta 54, 1801 (1971); D. Lamparsky and P. Schudel, Parfums, Mosmét. Savons Fr. 2, 465 (1972)). In particular, these revealed that menthon-thiol is the carrier of the "blackcurrent" note. Menthon-thiol is shown in patents (D. Lamparsky and P. Schudel, DT-OS No. 2 043 341, E. Sundt and G. Ohloff, CH-PS No. 543 584).

In the field of perfumery, only a limited number of oximes of aliphatic aldehydes or ketones with 7-10 carbon atoms are known (R. T. Dahill, U.S. Pat. No. 3,637,533, Jan. 25, 1972; i.e. DT-PS No. 1,692,002). These aldehydes and ketones (e.g. 2-methyl-2-hepten-6-one, citronellal) are common fragrance chemicals with fruity or citrus notes. The scent of the associated oximes differs from this and has been characterised as "green-leafy", "green-earthy" "flowery".

PREFERRED EMBODIMENTS OF THE INVENTION

No particular olfactory properties are known for the oximes of mono- or polycyclic ketones. It is thus surprising and novel that the newly produced compound 2 has an intense fresh, fruity-green fragrance with a distinct "blackcurrent" note. This was particularly surprising in view of the fact that the ketone 1 and the ketals thereof merely posses herbal, earthy notes. The special olfactory properties of compound 2 make it very suitable for use as a perfuming agent or constituent of perfume oils.

Compound 2 can also be used as a flavoring agent or a constituent of flavoring compositions.

The results of sensory evaluation were:

| | |
|---|---|
| Minimum detectable amount | 0.2 ppm (in sugar water) |
| Minimum quantifiable amount | 0.9 ppm |
| Flavor evaluation | sweet, dark-fruity, blackcurrent fuller and less fresh than buchu leaf oil |
| Flavor intensity | approx. 50% of buchu leaf oil approx. 5% of menthon-thiol |

The compound (2) in the invention is produced by reacting 1.5-dimethyl-bicyclo[3.2.1]octane-8-one (1) by a known method with hydroxylamine in the presence of strong bases, preferably sodium or potassium hydroxide or sodium or potassium acetate. Reaction preferably takes place at elevated temperature: a temperature up to the boiling point of the reaction medium may be used. However the preferred temperature lies in the range 50° C. to 75° C. The substance is prepared and isolated according to the usual methods used in industrial organic chemistry. The oxime 2 obtained in this way has a different melting point and IR data to the material described in DE-OS No. 2 945 812.

The invention is better illustrated by but not limited to the following examples:

EXAMPLE 1

Preparation of 1.5-dimethyl-8-hydroximino-bicyclo[3.2.1]octane (2)

At 60° C., 91.2 g (0.6 mole) of 1.5-dimethyl-bicyclo[3.2.1]octane-8-one (1) was dripped into a solution of 78.7 g (0.6 mole) hydroxylamin hydrogensulfate and 54.2 g (0.66 mole) sodium acetate in 135 g water. This was stirred for 1 h at 60° C. and then allowed to cool to room temperature and sodium extracted with ether. The combined organic phases were neutralized by washing with a saturated solution of chloride, dried and concentrated by evaporation. 95 g (95%) 2 crystalline solid is obtained. By crystallising 9 g of the raw product from 15 ml ethanol, 8 g 2 are obtained having a m.p. of 129°-130° C. IR: 3400, 3250, 1685, 930 $cm^{-1}$ (oxim). NMR ($CCl_4$): $\delta=1.05$, s ($-CH_3$, transoid to —C=N—OH), 1.43, s ($-CH_3$, cisoid to —C=N—OH), 9.03 ppm (—C=N—OH). MS: m/z (%)=167 ($M^+$, 2%), 150(85), 133(15), 123(17), 108(23), 93(100). $C_{10}H_{17}ON$ (M: 167.24)

EXAMPLE 2

| Perfume oil with oriental note | |
|---|---|
| Galbanum oil (10%) | 5 g |
| Vanillin (10%) | 20 g |
| p-hydroxyphenylbutanon-3 (10%) | 30 g |
| Maltol (1%) | 5 g |
| Civet natural (3%) | 20 g |
| Undecylenaldehyd (10%) | 30 g |
| Cyclohexyl oxy acetic acid allyl ester | 30 g |
| Ambergris tincture (5%) | 10 g |
| Mandarine oil, Italian | 15 g |
| Bergamot oil, Reggio | 30 g |
| Benzyl acetate | 30 g |
| Phenyl ethyl alcohol | 30 g |
| Citronellol | 10 g |
| Oil of roses, Bulgarian | 10 g |
| Rose de Mai, absolue | 10 g |
| Hydroxycitronellol | 50 g |
| Cedryl acetate | 150 g |
| Vetiveryl acetate | 70 g |
| Patchouli oil, Singapore | 150 g |
| Coumarin | 10 g |
| Musk ketone | 50 g |
| Benzyl salicylate | 85 g |
| Iso eugenol methyl ether | 20 g |
| Ylang-Ylang oil | 20 g |
| Coriander oil | 10 g |
| Styrolyl acetate | 10 g |
| Tarragon oil | 5 g |
| Benzoe Siam Resinoid | 20 g |
| Oak moss, Jugoslavia | 10 g |
| Labdanum extract | 5 g |
| Methyl ionone, gamma | 50 g |

-continued

| Perfume oil with oriental note | |
|---|---|
| Styrax extract | 10 g |
| alpha-methyl cinnamaldehyde | 30 g |
| | 1108 g |

The above perfume oil has an oriental fragrance with flowery, woody notes. Flowery-fruity notes are emphasised by adding 20 parts of compound 2, and the composition is complemented as desired by a buchu note, which is otherwise only achieved to some extent by means of "Cassis bourgeous".

Compound 2 may be used as odorant in pure form. As component of perfume oils or flavor compositions the usual concentration is 0.001 to 30%, preferably 0.1 to 20%. All percent given are percents by weight.

What we claim is:

1. Process for imparting, enhancing or modifying the odorous note of a material selected from the group consisting of perfumes and perfume compositions by imparting a blackcurrant note, which comprises adding thereto a 1,5-dimethyl-8-hydroximinobicyclo3,2,1octane, at a concentration of at least 1 part per million by weight based on the total weight of the thus obtained material.

2. Process according to claim 1, wherein the compound is used in an amount of at least 10 parts per million.

3. A process as defined in claim 1 wherein the material is a perfume.

4. A process as defined in claim 1 wherein the material is a perfume composition.

* * * * *